United States Patent
Copelan et al.

(10) Patent No.: US 10,220,255 B2
(45) Date of Patent: Mar. 5, 2019

(54) WEARABLE MEASURING APPARATUS FOR SPORTS TRAINING

(71) Applicants: Russell Copelan, Pensacola, FL (US); Lori Copelan, Pensacola, FL (US)

(72) Inventors: Russell Copelan, Pensacola, FL (US); Lori Copelan, Pensacola, FL (US)

( * ) Notice: Subject to any disclaimer, the term of this patent is extended or adjusted under 35 U.S.C. 154(b) by 9 days.

(21) Appl. No.: 15/951,668

(22) Filed: Apr. 12, 2018

(65) Prior Publication Data

US 2018/0296878 A1  Oct. 18, 2018

Related U.S. Application Data

(60) Provisional application No. 62/484,802, filed on Apr. 12, 2017, provisional application No. 62/707,583, filed on Nov. 8, 2017.

(51) Int. Cl.
*G01B 7/30* (2006.01)
*G06F 1/16* (2006.01)
*A63B 24/00* (2006.01)

(52) U.S. Cl.
CPC ...... *A63B 24/0006* (2013.01); *A63B 24/0062* (2013.01); *G01B 7/30* (2013.01); *G06F 1/163* (2013.01); *G06F 1/1694* (2013.01)

(58) Field of Classification Search
CPC . A63B 24/00; A63B 24/0003; A63B 24/0006; A63B 24/0021; A63B 24/0062; A63B 2024/0009; A63B 2024/0012; A63B 2024/0025; A63B 2024/0068; A63B 2024/0071; A63B 71/06; A63B 71/0619; A63B 71/0622; A63B 71/0686; A63B 2071/0625; A63B 2071/0627; A63B 2071/063; A63B 2071/0636; A63B 2071/0647; A63B 2071/065; A63B 2071/0652; A63B 2071/0655; A63B 2071/0658; A63B 2071/0661; A63B 2071/0663; A63B 2071/0675; A63B 2071/0677; A63B 2071/068;
(Continued)

(56) References Cited

U.S. PATENT DOCUMENTS

5,930,741 A * 7/1999 Kramer ............. A63B 69/3608
340/524
7,625,316 B1 * 12/2009 Amsbury .......... A63B 24/0062
482/1
(Continued)

*Primary Examiner* — Gary D Urbiel Goldner
(74) *Attorney, Agent, or Firm* — Venjuris, PC (57) ABSTRACT

A wearable apparatus for using reinforced neurofeedback for sports training is configured to be worn at or near a user's joint to monitor a position of the user's joint. One such a wearable apparatus comprises a processor, a computer-readable medium, a sensor, an I/O component, a battery, a timer, a signaling component, and a flexible printed circuit. The computer-readable medium store at least one optimal range of the user's joint and/or a sequence of timed optimal ranges of the positions of the user's joint for a specific sport. The sensor continuously detects the position of the user's joint. Once the processor determines that the user's joint falls outside the optimal range of the position of the user's joint, the processor activates the signaling component to send a feedback signal for the user to make immediate corrections to the position of the user's joint.

7 Claims, 5 Drawing Sheets

(58) Field of Classification Search
CPC .... A63B 2071/0683; A63B 2071/0694; A63B 2220/10; A63B 2220/13; A63B 2220/16; A63B 2220/17; A63B 2220/40; A63B 2220/44; A63B 2220/62; A63B 2220/80; A63B 2220/801; A63B 2220/802; A63B 2220/803; A63B 2220/805; A63B 2220/806; A63B 2220/807; A63B 2220/83; A63B 2220/836; A63B 2225/15; A63B 2225/20; A63B 2225/50; A63B 2225/52; A63B 2225/54; G01B 7/30; G06F 1/163; G06F 1/1694
See application file for complete search history.

(56) References Cited

U.S. PATENT DOCUMENTS

| | | | | |
|---|---|---|---|---|
| 8,449,410 | B1* | 5/2013 | Kaufman | A63B 49/08 |
| | | | | 473/459 |
| 8,465,382 | B2* | 6/2013 | Moye | A63B 24/0006 |
| | | | | 473/422 |
| 9,161,708 | B2* | 10/2015 | Elliott | A63B 71/06 |
| 9,772,684 | B2* | 9/2017 | Shi | G06F 3/011 |
| 9,773,330 | B1* | 9/2017 | Douglas | G06T 11/206 |
| 2003/0120183 | A1* | 6/2003 | Simmons | A61F 4/00 |
| | | | | 600/595 |
| 2007/0066415 | A1* | 3/2007 | Hou | A63B 69/3608 |
| | | | | 473/219 |
| 2011/0021318 | A1* | 1/2011 | Lumsden | A63B 69/00 |
| | | | | 482/8 |
| 2012/0157263 | A1* | 6/2012 | Sivak | G06F 3/014 |
| | | | | 482/4 |
| 2012/0190505 | A1* | 7/2012 | Shavit | A63B 71/0622 |
| | | | | 482/8 |
| 2015/0048849 | A1* | 2/2015 | Reese | A61B 5/1071 |
| | | | | 324/671 |
| 2016/0051879 | A1* | 2/2016 | Reynolds, III | A63B 69/0028 |
| | | | | 700/91 |
| 2016/0077581 | A1* | 3/2016 | Shi | G06F 3/011 |
| | | | | 340/12.5 |
| 2016/0089571 | A1* | 3/2016 | Wesley | A61B 5/1071 |
| | | | | 482/8 |
| 2016/0322078 | A1* | 11/2016 | Bose | G11B 27/031 |
| 2016/0338644 | A1* | 11/2016 | Connor | A61B 5/6804 |
| 2016/0367879 | A1* | 12/2016 | Reynolds, III | A61B 5/7415 |
| 2017/0000386 | A1* | 1/2017 | Salamatian | A61B 5/742 |
| 2017/0039882 | A1* | 2/2017 | Hashimoto | A61B 5/1127 |
| 2017/0060298 | A1* | 3/2017 | Hwang | A61B 5/6807 |
| 2017/0123487 | A1* | 5/2017 | Hazra | G06F 3/015 |
| 2017/0182360 | A1* | 6/2017 | Chang | G06F 7/02 |
| 2017/0189784 | A1* | 7/2017 | Sasaki | A63B 69/3667 |
| 2017/0197111 | A1* | 7/2017 | Mak | A63B 24/0006 |
| 2017/0203154 | A1* | 7/2017 | Solinsky | A63B 24/0006 |
| 2017/0225033 | A1* | 8/2017 | Czaja | A63B 24/0006 |
| 2017/0229154 | A1* | 8/2017 | Bose | G11B 27/34 |
| 2017/0272842 | A1* | 9/2017 | Touma | H04Q 9/00 |
| 2017/0308117 | A1* | 10/2017 | Park | G06F 1/163 |
| 2017/0308118 | A1* | 10/2017 | Ito | G06F 1/163 |
| 2017/0312576 | A1* | 11/2017 | Natarajan | A63B 24/0062 |
| 2017/0354843 | A1* | 12/2017 | Vuillerme | A63B 24/0003 |
| 2018/0015345 | A1* | 1/2018 | Wrigg | A63B 69/00 |
| 2018/0021647 | A1* | 1/2018 | Wrigg | A63B 69/00 |
| 2018/0028862 | A1* | 2/2018 | Statham | A63B 24/0006 |

* cited by examiner

WEARABLE MEASURING APPARATUS FOR SPORTS TRAINING

CROSS-REFERENCE TO RELATED APPLICATIONS

This application claims priority to the co-pending U.S. provisional application No. 62/484,802, entitled WEARABLE APPARATUS AND METHOD FOR SPORTS TRAINING, filed Apr. 12, 2017, and the U.S. provisional application No. 62/707,583, entitled WEARABLE DISPOSABLE SPORTS TRAINING APPARATUS, filed Nov. 8, 2017. The entirety of these provisional applications is incorporated by reference.

BACKGROUND

For many sports, including but not limited to golf, archery, shooting, basketball free throw, explosive track and swim block starts, that utilize a dominant or non-dominant arm or leg, alone or in combination, there exits only a basic number of optimal, preloaded joint position platforms. Since hiring a personal trainer to monitor all the joint positions of a player while training would not be affordable for most people, it is desirous to have a wearable training apparatus that determines, in real time, whether a joint position is restricted or exceeds a predetermined range of optimal position and activates sensory training cues accordingly.

As an example, the myriad of golf training aids may attest to the difficulty of the sport. A vast array of expensive sports electronic wearable technology is described in the prior art focusing on golf course layout, GPS positioning, swing tempo, and ambulatory steps taken, none of which has demonstrated score improvement. In addition, existing wearable training devices for golf training, including impact sliders, speed sticks, flexible cords, static glove inserts, synchronous balls, trigger grips, smart finger pads, and rigid wrist angle positioners, are designed for training a single motion only and cannot be adjusted based on the player's skill level. It is thus desirous to have a multifunctional wearable training apparatus that can be adjusted based on its intended uses, such as the sport, the user's skill level, and the motion to be trained.

SUMMARY

The structure, overall operation and technical characteristics of the present invention will become apparent with the detailed description of preferred embodiments and the illustration of the related drawings as follows.

The invention is incorporated in wearable apparatuses and methods for using reinforced neurofeedback for sports training. Embodiments of such wearable apparatuses are configured to be worn at or near a user's joint, such as a wrist based epidermal wearable patch. A first preferred embodiment of the wearable apparatus comprises a processor, a computer-readable medium, a sensor, an input/output ("IO") component, a battery, a timer, a signaling component, and a flexible printed circuit board (the "flex circuits").

A second preferred embodiment of the wearable apparatus comprises a flexible middle layer enclosed between an anterior protective layer and a posterior protective layer. The second embodiment is configured to provide feedback to a user based on the middle layer's specific characteristics, such as kinking, buckling, or breaking when the embodiment is bent or twisted to different predetermined degrees with the joint.

First Preferred Embodiment of a Wearable Apparatus

In this first preferred embodiment, the computer-readable medium is configured to store instructions to be executed by the processor and at least one optimal range of joint position and/or a sequence of timed optimal ranges of joint positions for a specific sport, depending on what kind of training is needed. If this embodiment is used for training a single position, then an optimal range of joint position is stored at the computer-readable medium. If a sequence of movements is to be monitored, such as a golf swing, this embodiment may store a sequence of timed optimal ranges of joint positions, each including an optimal range of joint position, i.e. a range of angular tolerances, and a corresponding timecode preferably starting from zero.

Alternatively, an embodiment may be used for various trainings, some monitoring a single position while others monitoring sequences of movements. That is, the different sets of optimal range of joint position and timed optimal ranges of joint positions of such an embodiment may additionally be tagged for the associated sports, techniques, skill levels, joints to monitor, and so forth. The at least one optimal range of joint position or timed optimal ranges of joint positions in an embodiment can be predetermined by factory settings or altered by a user via the IO component. In an alternate embodiment, user training records may also be stored at the computer-readable medium as well for analysis of the training progress by a remote computer or server.

In the preferred embodiment, the sensor is configured to measure the relative angles of a joint at a wrist, an elbow, a shoulder, a knee, or an ankle along at least one of the three axes of an orthogonal or Cartesian coordinate system (XYZ) attached to a mobile or body frame of reference, yet basically fixed body. Examples of the sensor of the preferred embodiment include a three-axis goniometer and/or accelerometer combination, an optical motion tracking system, and so forth. In an exemplary embodiment with at least two accelerometers for monitoring a wrist position, the embodiment is preferably attached across the wrist crease line, with at least one accelerometer attached at the back of the hand and at least one accelerometer attached to the forearm. In such an embodiment, the wrist position is thus determined by the relative angle between the hand and the forearm based on the readings of the accelerometers.

An alternate embodiment may further include one or more sensors configured to monitor a user's vital signs, including heart rate, breathing rate, and/or skin temperature. These vital signs may provide additional feedbacks for training for some sports, such as archery, shooting, bowling, free throw shooting, and golf, wherein increased heart rate associated muscle quivering or other autonomic physiologic artifact may decrease precision.

When this preferred embodiment is used to monitor a single joint position, if the processor determines that the joint position falls outside the optimal range of joint position, the signaling component is activated to send a signal to the user. Alternatively, when this preferred embodiment is used to monitor a sequence of movements, the embodiment may repeat the following exemplary steps until the user stops the embodiment or it enters a sleep mode or automatically shuts down:

Step 1: the processor retrieving a current time from the timer;

Step 2: the processor checking if a timecode of one of the timed optimal ranges stored in the computer-readable medium matches the current time, and going back to Step 1 if no match;

Step 3: the processor retrieving a joint position detected by the sensor;

Step 4: the processor determining whether the joint position falls outside the timecode's corresponding optimal range of joint positions, and goes back to Step 1 if the joint position is inside the optimal range; and Step 5: the processor activating the signaling component.

In this preferred embodiment, joint movements and joint positions may be classified as Tait-Bryan or classic Euler angles. For instance, when this embodiment is used for golf swing training, the predetermined optimal time for the whole motion follows a 3 to 1 ratio, that is, backswing time to downswing time, in an approximately 1.5-second period. The putting motion follows a 1 to 1 ratio in an approximately 1-second period. An exemplary set of timed optimal joint positions for this embodiment used in golf putting training may have:

- a first angular value (0°, 0°, 0°), i.e. the wrist's three elemental rotations about the axes of the XYZ system of the forearm, at the beginning (timecode=0);
- a second angular value (0°, 15°, 0°) in the middle (timecode=0.5 second);
- a third angular value (0°, 30°, 0°) at the end (time code=1 second); and
- the acceptable ranges are (±5°, ±10°, ±5°).

Below are some examples of common acceptable ranges of joint positions (wrist/frame angles):

- Golf Setup: In an orthogonal coordinate system (XYZ), the optimal range of ulnar deviation from neutral X of the leading swing arm ($\theta_1$) may be 0° up to 10°, while the wrist extension from neutral Y ($\theta_2$) is 0° up to 5°, and the pronation from neutral Z ($\theta_3$) is between 0° to 5°, depending on whether the grip is weak or strong.
- Golf Club Takeaway: Generally, when golfers correctly hold a club at the time of cocking their wrists early in the swing, the optimal range of ulnar deviation from neutral X of the leading swing arm ($\theta_1$) equals up to 20°, the wrist extension from neutral Y ($\theta_2$) is up to 5°, and the pronation from neutral Z ($\theta_3$) is ±1° to 2°. Greater angles for Y and Z will increase compensatory to decreases in X, commonly referred to cupping or bowing of the wrist with loss of a square club face in the arc of the swing.
- "Straight" Bowling Wrist Positions: There are many different hand positions in bowling. The basic vertical hand positions include Cupped, Straight, and Broken. At the "straight" position, often used as a starting point, the heel of the hand (intrinsic thenar muscles of the thumb) remains in a straight line with the bowling arm and with the back (dorsum) of the wrist, and an optimal range of wrist position ($\theta_1$, $\theta_2$, $\theta_3$) for starting bowlers can be (±1°~5°, ±1°~5°, 90°±0°~5°).

As to the IO component of the preferred embodiment, it is configured to receive a user command, which may be as simple as instructions such as power-on, power-off, start, reset, and stop, or as complicated as instructions plus data such as upgrading firmware, downloading revised or additional (timed) optimal ranges of joint positions, uploading user training records, and so on. Examples of the IO component may include a power button configured to turn on or off the embodiment; a selection button configured for the user to select a sport for training, a technique of the selected sport, a skill level, or an angular tolerance; a touch screen configured to receive user instruction; a device communicably coupled to the embodiment via a USB port, Wi-Fi, or Bluetooth, such as a smart phone, a computer, or a server; and any commercially available input/output devices, as well as combinations thereof.

The battery of the preferred embodiment can be a cell battery, a solar battery, or any type of power source as long as it is properly sized and can provide sufficient electric power to all the components in the embodiment. An exemplary battery can be non-rechargeable or rechargeable, by a traditional battery charger, an inductive charger, or any suitable wired or wireless charging device. As stated above, the preferred embodiment may enter a sleep mode or automatically shut down to save power. Specifically, the preferred embodiment may shut down automatically when a predetermined time elapses after the embodiment first becomes inactive, i.e. when the sequence of movements to be monitored is over, or no more movements are detected, without any further user commands.

Additionally, the preferred embodiment may include a flex circuit that electrically connects all the components and has a side with refastenable, skin-safe adhesive for releasably coupling the user's joint. In another embodiment, the embodiment may include a case configured to be releasably coupled to the user's joint. Examples of such a case include a glove, a wrist band, and so forth.

Furthermore, in the preferred embodiment, the signaling component is configured to send a sensory cue or signal to the user, which may be in the form of sound, light, vibration, image, text, or combinations thereof. The signaling component of the preferred embodiment may be activated when either the joint movement is outside or inside the optimal range of positions, depending on the setting, or when the battery is low. For instance, the signaling device of an embodiment worn on a user's wrist may beep when the position of the user's wrist is outside the predetermined range of optimal position and stop beeping until the wrist position gets back into the range. Alternatively, another embodiment may comprise three signaling devices—three LED lights of different colors, each configured to show whether the joint position is inside the optimal range at a corresponding axis. In yet another embodiment, the signaling component may include haptic or mechanical stimulation or a display screen configured to show warning messages, flashing light, instructions, or a symbol when the joint position is outside or inside the optimal range of joint position or when the battery power is low. Moreover, an embodiment can be made of any suitable materials—preferably made, entirely or substantially, of compostable, biodegradable, and eco-friendly materials.

Second Preferred Embodiment of a Wearable Apparatus

The second preferred embodiment comprises a middle layer or sheet made of flexible, fibrous, lignified material, such as balsa wood. In this embodiment, the middle layer, corresponding to the fibrous microstructure, is enclosed in two flexible protective layers, such as vellum, to maintain integrity and prevent the middle layer from splintering. A similar embodiment may instead include a flexible protective sheath to enclose the middle layer. Such an embodiment is preferably disposable, biodegradable, and eco-friendly.

Naturally occurring balsa wood is a suitable material for the middle layer of such an embodiment because it has excellent stiffness-to-weight and strength-to-weight ratios as well as superior energy absorption characteristics. These properties of dimension, weight, density (e.g., ultra light, light), and grain types (A, B, C-grain) are derived from its geometric microstructure and may determine the rigidity or flexibility of a balsa sheet.

Densities of balsa sheets are generally classified as:

| Grade | Ultra Light | Light | Light Medium | Medium | Medium Hard | Hard |
|---|---|---|---|---|---|---|
| Density in lb/cu.ft | 4-5.4 | 5.5-6.0 | 6.1-7.5 | 7.6-9.5 | 9.6-12 | 14+ |

Additionally, balsa sheets are often classified, based on the grain types, into A, B, and C-grain. A-grain balsa sheet has long fibers and is very flexible along the width of the sheet. It is commonly used for bending around objects. C-grain balsa sheet has shorter, more mottled grain, and is stiff, brittle, and splits easily. B-grain sheet is in between and serves as an all-purpose balsa item.

Under shear stress, specifically axial/tangential (A/T) stress, balsa wood demonstrates an elastic regime that terminates by the initiation of failure in the form of localized kinking, buckling, or breaking that alerts the golfer accordingly by feeling the swing breakpoint. Additionally, the direction of the kinking, buckling, or breaking may provide additional information as to the joint motion—excessive roll movements (Z or tangential, roll Cartesian coordinate) confirming angular break, excessive wrist flexion (palmar flexion)/extension (dorsiflexion) travel (Y or axial, pitch Cartesian coordinate) demonstrating parallel break, and so forth. The distinct biomechanical properties of balsa wood, in axial, tangential, and radial directions, make it an advantageous material for a naturally occurring substrate in an embodiment for measuring dynamic motions and positions. Indeed, in this second preferred embodiment, the middle layer is made from a C-grain, light-density balsa sheet.

As an illustration, departure angles from wrist position neutral, greater than $5°±2°$ degrees extension (dorsiflexion) to $5°±2°$ degrees flexion (palmar flexion) during the golf swing are acceptable in this preferred embodiment. At these shear strain angles, each response develops a stress maximum that is considered as the value at which kinking in the Axial-Tangential (A/T) plane will initiate in this embodiment. Greater angles of flexion (palmar flexion) or extension (dorsiflexion) will result in complete microstructure breakpoints. That is, when the second preferred embodiment is attached to the wrist of a golfer's leading arm, the middle layer can be configured to break when the angel of flexion (palmar flexion) or extension (dorsiflexion) exceeds the optimal range of joint position along X axis, $5°±2°$. An alternate embodiment may be configured to permanently change its physical properties (after kinking, buckling, or breaking) at alternate degrees based on the dimension, weight, density, and/or grain types of its middle layer.

Embodiments of a Sport Training Method

A preferred embodiment of a method for using real-time feedback for sports training comprises the steps of:
Step 1: Detecting a joint position of a user's joint by the sensor releasably attached to the joint and;
Step 2: Determining by a processor in real time whether the joint position is outside a predetermined range of optimal joint position retrieved from a computer-readable medium; and
Step 3: If the processor determines that the joint position is outside the predetermined range of optimal joint position and a perceivable alert signal is not activated, then activating the signal and going back to Step 1, otherwise deactivating the signal.

Another preferred embodiment of a method for sports training comprises the steps of:

Step 1: Detecting a 3-dimensional joint position of a user by sensor;
Step 2: Matching a timestamp retrieved from a timer to a timecode retrieved from a computer-readable medium by a processor;
Step 3: Determining by the processor in real time whether the joint position is outside the timecode's corresponding optimal range of joint position stored in the computer readable medium; and
Step 4: If the joint position is outside the predetermined optimal range of joint position and a perceivable signal is not activated, then activating the signal and going back to Step 1, otherwise deactivating the signal.

An alternate embodiment of a method for sports training may additionally include one or more of the steps of receiving user command to start, stop, or reset; communicably coupling, through wire or wirelessly, to a device for receiving or transmitting data including the detected joint positions, user command, the timed optimal range of joint positions, and user settings; and so forth.

One object here is to provide wearable apparatuses and methods for improving sport specific joint angle positions and performance by giving out a real-time warning signal when the user's joint position is not within a predetermined optimal range.

Another object is to improve sport performance by tracking and recording the user's joint movements for analysis and training purposes.

DESCRIPTION OF THE EMBODIMENTS

Embodiments of a wearable apparatus for tracking and improving sports performance are illustrated in FIGS. 1-5. The preferred embodiment 100 in FIGS. 1-2 comprises a microprocessor that includes a processor 110, a computer-readable medium 120 storing computer instructions and at least one predetermined set of optimal ranges of joint positions, and a timer 160. The embodiment 100 further comprises two sensors (accelerometers) 130 configured to detect a joint position, i.e. a relative angle of the joint, determined based on the readings of the two sensors 130; an IO component 140, i.e. an on/reset switch; a battery 150; two signaling components 170, including an LED and a vibrator; and a flex circuit 180 with a layer of refastenable, skin-safe adhesive 181 at its back/bottom side.

This embodiment 100 is configured to be releasably coupled to any joint of a user, preferably by the adhesive 181 at the back of the flex circuit 180 or by any suitable fastener. The dimensions of this embodiment 100 are 1"×3"×0.12". In another embodiment, the flex circuit 180 may be substituted by any suitable flexible layer backing or printed circuit boards with proper wirings.

Additionally, this embodiment 100 is configured to be powered by the cell battery 150, which can alternatively be any suitable power source such as flexible solar cells. The switch 140 (i.e. the IO component) in this embodiment 100 is configured to turn on the embodiment 100 (see, step S100 in FIG. 2) or reset the time of inactivity, which may be a value stored at the computer-readable medium 120. In order to save battery power, the embodiment 100 is configured to automatically shut down after a predetermined time of inactivity, e.g. 5 minutes from the last time the switch 140 is depressed (see, steps S120 & S199 in FIG. 2). When the embodiment 100 is on, the LED (the signaling component 170 on the left of FIG. 1A) is configured to flash once per second.

Figure 1A:
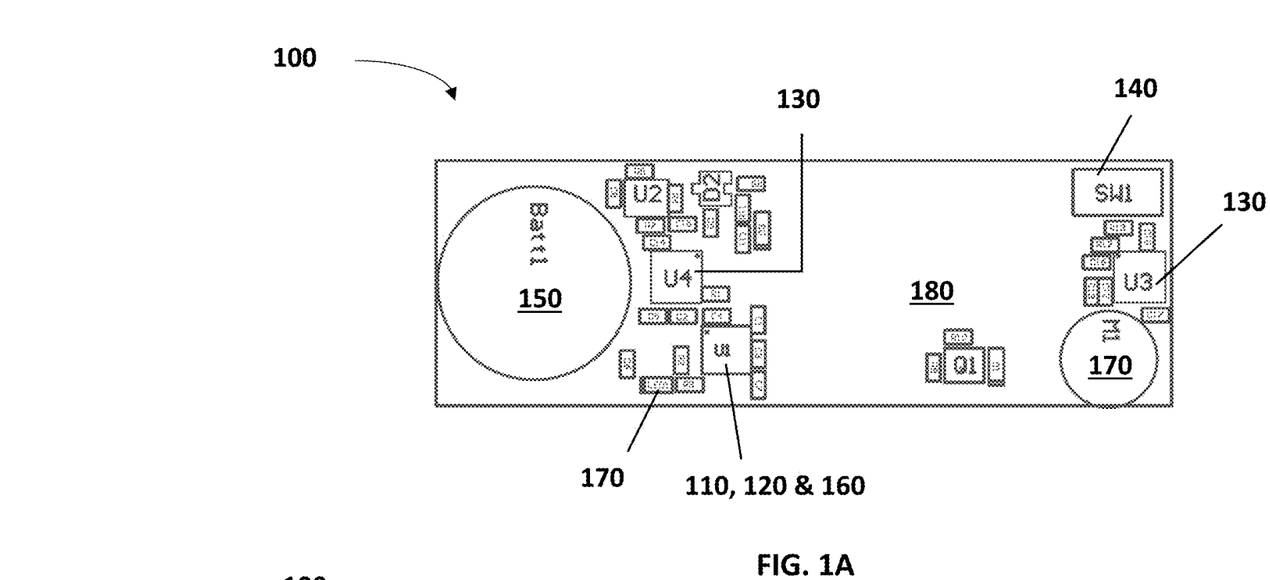
FIGS. 1A and 1B respectively show the top and front views of an exemplary wearable apparatus.
Figure 1B:
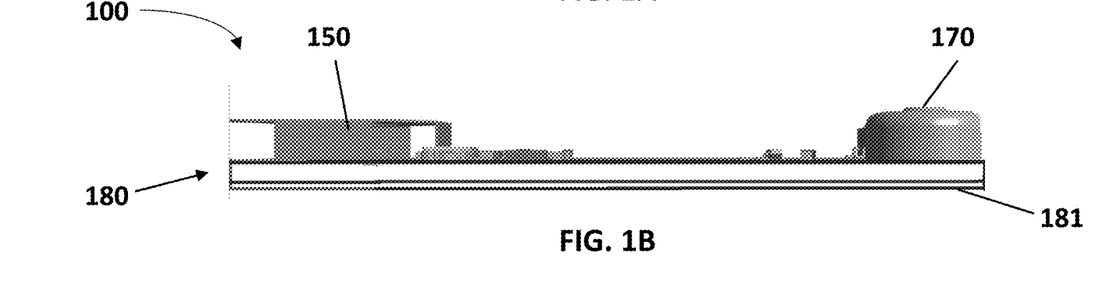

When this embodiment 100 is attached to the back of, and across, a user's wrist by the adhesive 181 it is possible to detect the wrist's joint position for golf swing training. Specifically, the sensor 130 on the right of the embodiment 100 in FIG. 1A is preferably located at one side of the wrist, e.g., the hand, and the other sensor 130 on the left is preferably located at the other side of the wrist, e.g., the forearm, or vice versa. The sensors 130 of this embodiment 100 are configured to continuously detect the joint position, i.e. the relative angle between the hand and the forearm.

Figure 2:
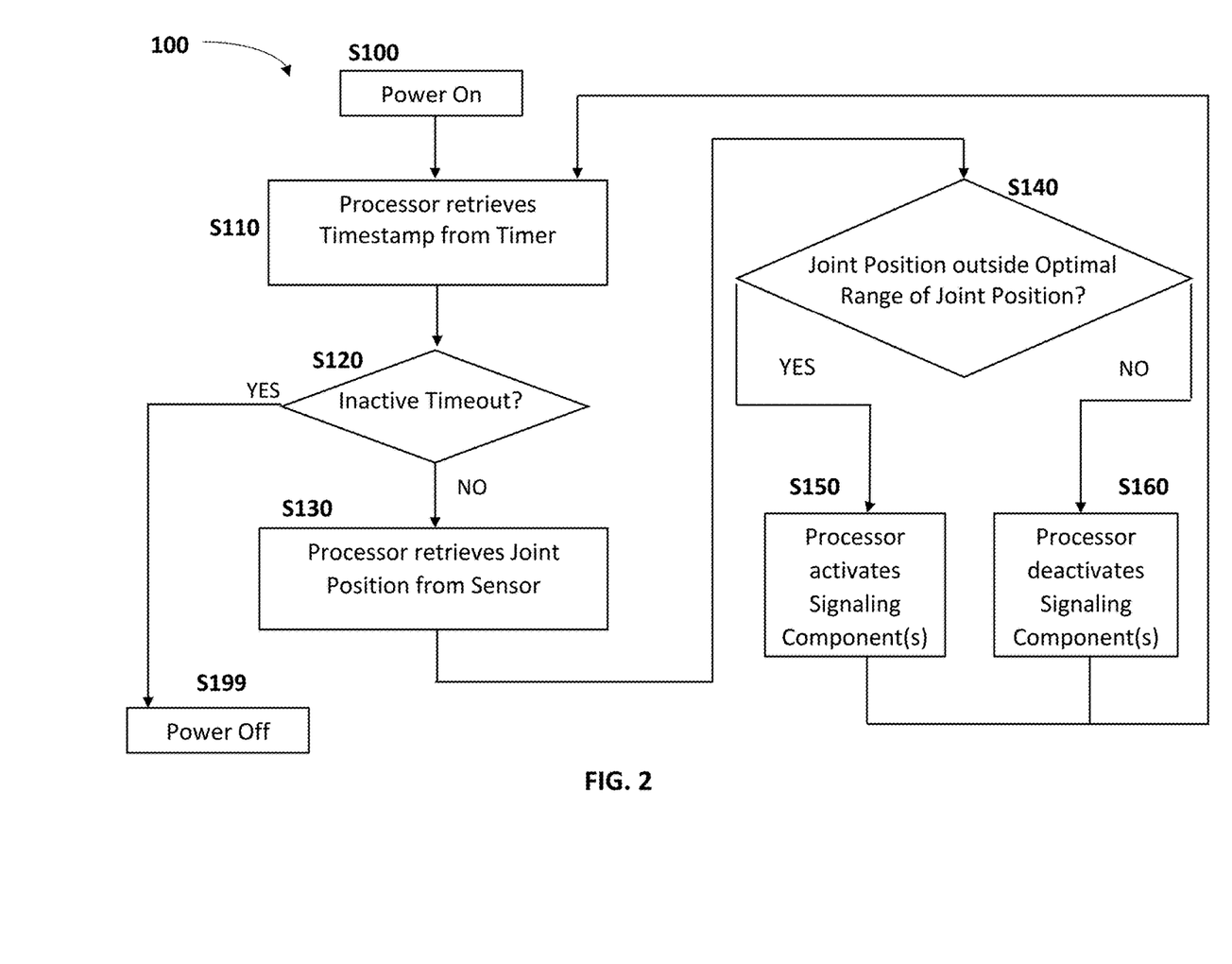
FIG. 2 shows the flow chart of how the exemplary wearable apparatus in FIG. 1 detects whether a user's joint is within the optimal range of joint position and signals the user if not.

As shown in FIG. 2, if the initial joint position (retrieved at step S130) is outside the optimal range of joint position (S140), the signaling components 170 of this embodiment 100 are activated (S150) to send feedback/warning signals— e.g. the LED 170 is configured to flash faster than usual (every 100 msec. for 1 second) and the vibrator 170 is configured to vibrate for 500 msec. The signaling components 170 in this embodiment 100 are not deactivated until the joint position is acceptable (S140→S160) or the embodiment is turned off (S199). Once the user corrects his/her joint position after perceiving the feedback signals, the new joint position is detected by the sensors 130 of this embodiment 100, and the processor 110 deactivates the signaling components 170 if the new position is within the optimal range of joint position.

In an exemplary use, a right-handed golfer's left leading wrist is monitored by this embodiment 100 for putting. A golfer basically must maintain the wrist angle throughout a putting stroke. Hence, an exemplary optimal range of joint position based on an orthogonal coordinate system may be (±10°, ±10°, ±1°). Alternatively, an optimal range of joint position may be a combination of allowed deviations on the orthogonal coordinate system, such as ±21°, i.e. the combinations of the ranges in the previous example.

As shown in FIG. 2, the embodiment 100 does not stop the loop of detecting the joint position and sending the feedback/warning signals (S110→S120→S130→S140→S150) until the user's joint position falls within the optimal range of joint position or the embodiment 100 has been inactive for too long (S120→S199). In another embodiment, the signaling component(s) may be deactivated after the signals, e.g. flashing light, sound, or vibration, are sent for a predetermined time, regardless of whether the user corrects the joint position.

The optimal ranges of joint positions, i.e. relative joint angles, adopted in this embodiment 100, may be hypothesized from observations, and preferably verified from 3D motion analysis and Trackman analytics research, and incorporated to mimic optimal flexion/extension wrist loads in the golf swing for novice through experienced players. Wrist movements may be classified as Tait-Bryan or classic Euler angles. Yaw, pitch, and roll can represent intrinsic rotations or three elemental rotations that occur about the axes of the orthogonal coordinate system (XYZ) attached to the user's body frame. The axes of the original frame, the forearm side of the wrist in this example, are denoted as xyz, and the axes of the rotated frame, the dominant hand in this example, are denoted as XYZ. The XYZ system rotates, while xyz is deemed fixed for the purpose of calculating a joint position. Starting with XYZ overlapping xyz as shown in FIG. 3A, a composition of three rotations can be used to reach any target orientation for XYZ.

Figure 3A:
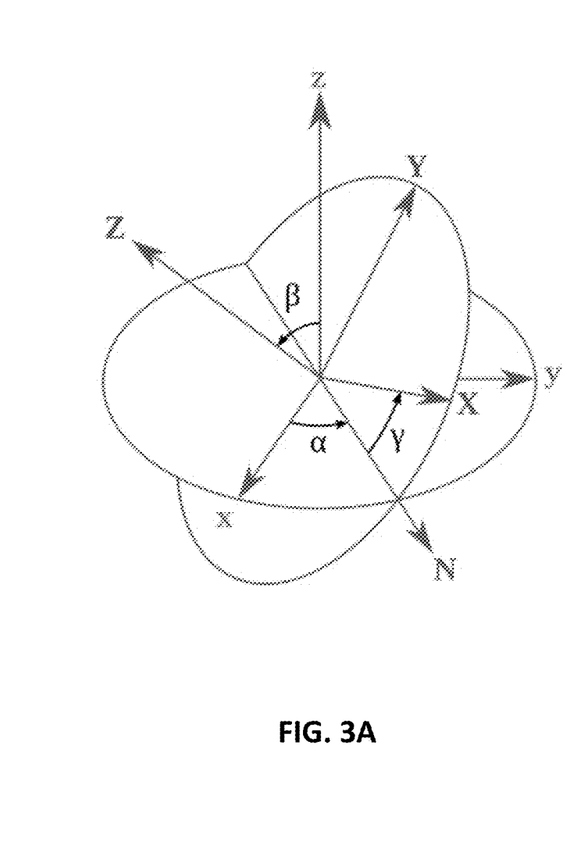
FIG. 3A shows three-dimensional rotational movements and the corresponding angle changes.

Proper Euler angles are defined geometrically in FIG. 3A, with a line or axis of reference (N). N denotes the internal or radioulnar axis line or a plane of reference. The Euler angles may be denoted $\alpha$, $\beta$, $\gamma$ as in FIG. 3A, or $\phi$, $\theta$, $\psi$, and defined as follows:

$\alpha$ (or $\phi$) is the angle between the x axis and the N axis.
$\beta$ (or $\theta$) is the angle between the z axis and the Z axis.
$\gamma$ (or $\psi$) is the angle between the N axis and the X axis.

The Euler angles ($\alpha$, $\beta$, $\gamma$, or $\phi$, $\theta$, $\psi$) are the amplitudes of these elemental rotations. Any target orientation can be reached, starting from a known reference orientation, using a specific sequence of intrinsic rotations, whose magnitudes are the Euler angles of the target orientation. The rotated frame XYZ may be imagined to be initially aligned with xyz, before undergoing the three elemental rotations represented by Euler angles. Its successive orientations can be derived. When rotations are performed in the right order for targeted or efficient threshold wrist orientations, the values of the rotation angles for these anatomical frames, e.g., preloaded setup, transition, or release positions, can be reached from the Euler angles.

Figure 3B:
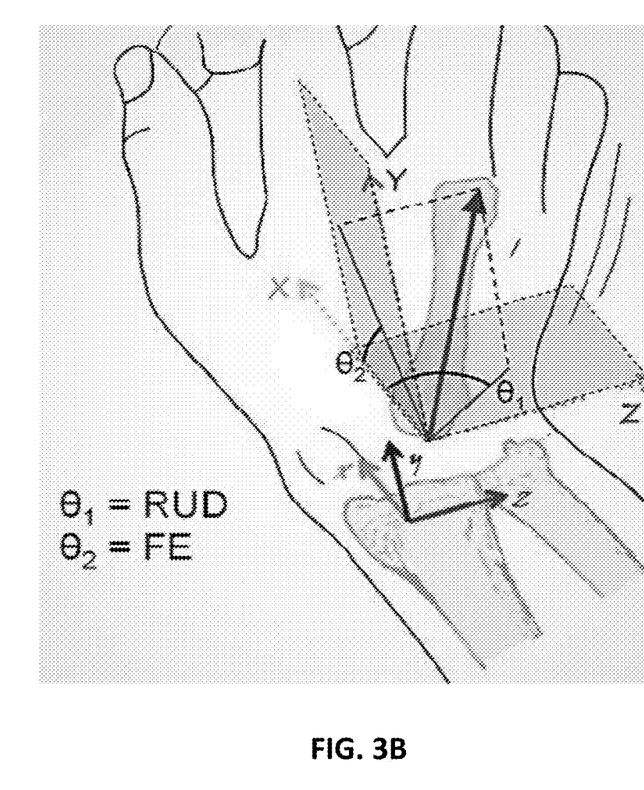
FIG. 3B shows an exemplary wrist positioning relative to a body or wrist frame.

By way of example, FIG. 3B represents a user's dominant hand with dynamic wrist positioning, generalizable to additional pre-loaded set-up platforms, that include predetermined biaxial radial-ulnar deviation (RUD) and flexion-extension positions (FE). This illustration shows the axes of the original body or wrist frame, represented as neutral 0-degree RUD and FE positions, and denoted as xyz. The axes of the rotated frame, the hand in this example, are represented as corresponding broken lines, XYZ, with 10-degree RUD and 20-degree FE orientations obtained from encoded $\theta_1$ and $\theta_2$ values. Also, the X axis in FIG. 3B, running through the base of the 3rd metacarpal, is comparable to the internal axis or reference body frame, i.e., radioulnar axis.

In another example at golf setup, up to 10° degrees of X (radial/ulnar, yaw, Cartesian coordinate RED) from neutral of the leading swing arm, with up to 10° degrees of Y (axial, pitch Cartesian coordinate GREEN) wrist extension from neutral, are acceptable, depending on the initial weak or strong grip of the leading hand. As an adjusted stronger grip is positioned beyond 5° degrees pronation from neutral Z (tangential, roll Cartesian coordinate BLUE) to increase Z, compensatory anatomical changes decreasing wrist extension angle Y (axial, pitch Cartesian coordinate) will result.

As another example, during golf club initial takeaway, 20° degrees of wrist X (radial/ulnar, yaw, Cartesian coordinate) deviation from neutral of the leading swing arm, with up to 5° degrees wrist extension Y (axial, pitch Cartesian coordinate) deviation from neutral, and up to 2° degrees Z (tangential, roll Cartesian coordinate) pronation from neutral are common angles that golfer's use to correctly hold the golf club at the time of cocking their wrists early in the swing. Greater angles for Y and Z will increase compensatory to decrease in X, commonly referred to cupping or bowing of the wrist with loss of a square club face in the arc of the swing.

A target orientation for set-up, transition or release wrist platforms can be reached and programmed, starting from a known reference wrist anatomic orientation, using a specific sequence of planned intrinsic rotations, whose magnitudes are the Euler angles of the target orientation. The rotated frame may be imagined to be initially aligned with the original fixed frame, before undergoing the three elemental rotations represented by Euler angles. Its successive orientations can be derived based on these values. The order of operations and direction of rotation may also be reversed.

For example, in the case presented in FIG. 3B, Euler angles are represented by $\theta_1$ (the radial-ulnar deviation), and $\theta_2$ (the flexion-extension positioning). These values provide a way to represent 3D orientation. The appropriate body frame or wrist platform is obtained by performing a rotation in degrees equal to the $\theta_1$ and $\theta 2$ values. Note that it is possible to reverse the order of operations and reverse the direction of rotation.

The embodiment 100 may additionally comprise an indicator (not shown) to show how to accurately position and secure the embodiment in place. As stated above, when the embodiment 100 is used to monitor a golfer's wrist, it is preferably coupled to the dorsal surface of the leading forearm, with the sensors 130 separated equidistantly, proximally and distally, from the dorsal wrist crease line and parallel to the long axis (X or radial/yaw Cartesian coordinate) of the leading forearm. In order to couple to the wrist, the embodiment 100 may be either adhered to the skin or slipped under the superior cuff of a snug fitting golf glove, in each case fastened by a pressure sensitive adhesive (i.e. the adhesive 181 in FIG. 1B).

Figure 4:
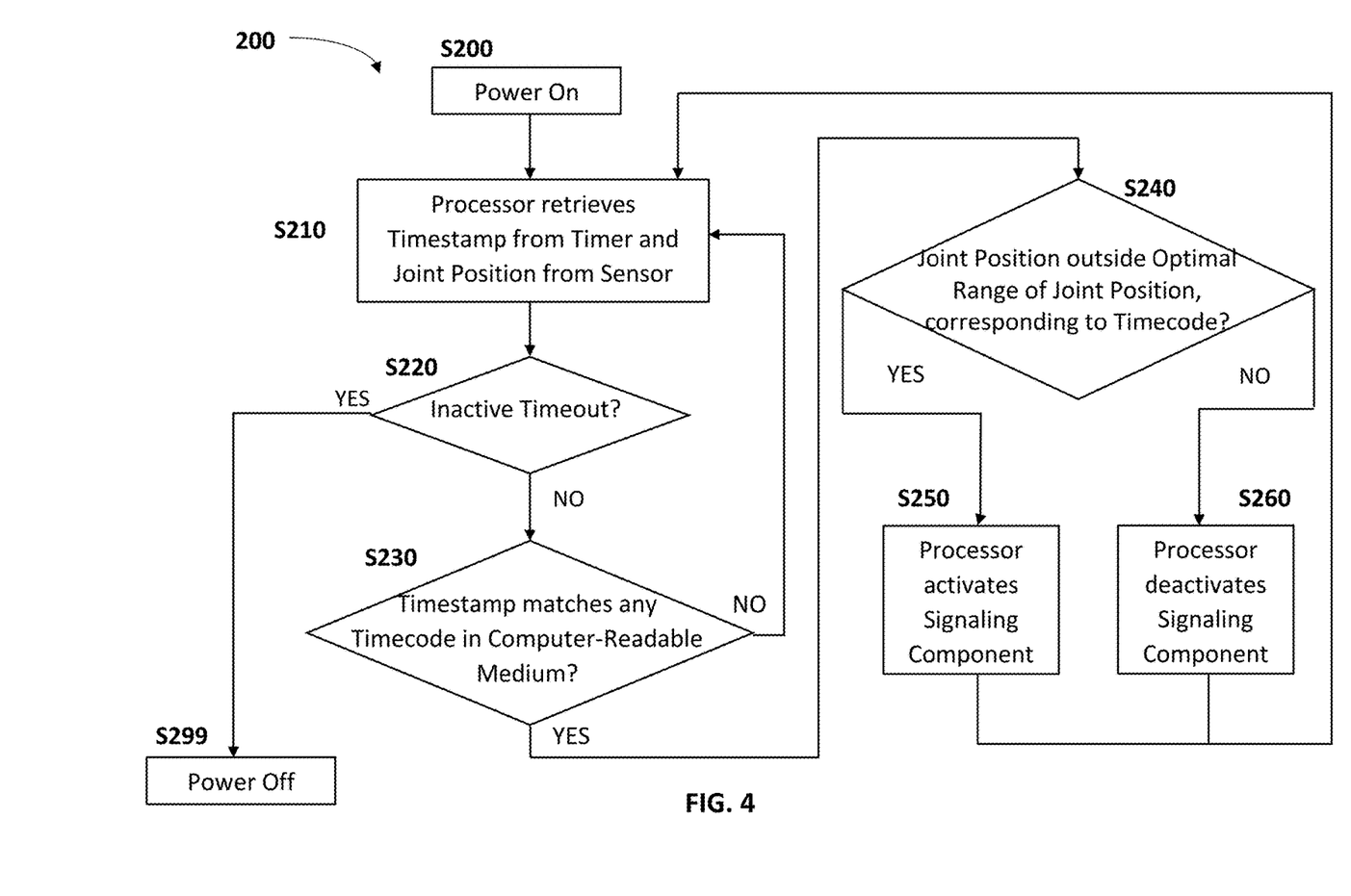
FIG. 4 shows the flow chart of how another exemplary wearable apparatus detects whether a user's joint movements conformed to the predetermined timed optimal ranges of joint positions.

An alternate embodiment 200 in FIG. 4 is configure for training one or more sequences of movements, such as a continuous swing motion, a golf putting motion, and so forth. The embodiment 200 may include similar components as in the embodiment 100. In this embodiment 200, the user's joint positions at different points of time are evaluated by the processor based on the timed optimal ranges of joint positions at steps S230-S240.

In an exemplary use, the X axis of a golfer's leading left wrist is monitored by this embodiment 200. An exemplary sequence of swing movements, i.e. a set of timed optimal ranges of joint positions (pairs of timecodes and optimal ranges of joint positions (ORJPs)), is stored at the computer-readable medium with 4 records with the first 2 records for the backswing and the last 2 records for the downswing:

| Timecode (msec.) | ORJP (X axis) |
|---|---|
| 0 | −15°~15° |
| 112 | −10°~10° |
| 130 | −5°~5° |
| 150 | −1°~1° |

The embodiment 200 may include similar components as in the embodiment 100 or further include a pause button for the user to train at a specific joint position, a select button for the user to choose from the multiple predefined sequences of movements based on the user's skill level, the joint to monitor, or the type of sports, or a reset button for the user to start from the initial position to the specific joint position that the user does wrong before. An alternate embodiment may receive user commands from a remote device (as an IO component) via Bluetooth, such as an app on a cell phone that remotely starts, pauses, or resets the embodiment worn by a golfer and controlled by the coach.

Figure 5A:
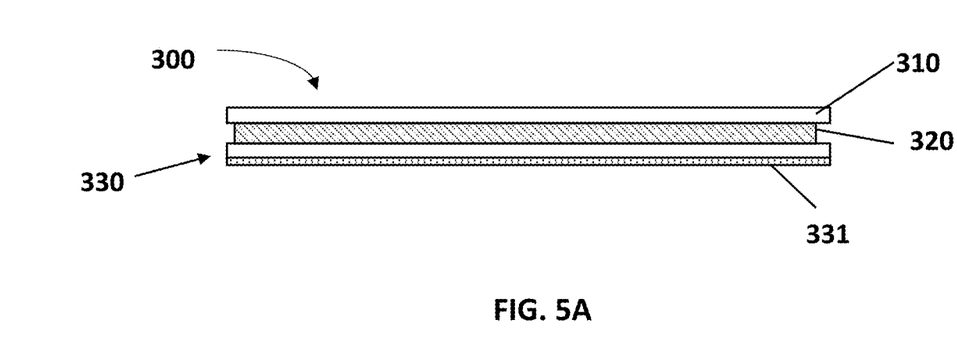
FIG. 5A shows a cross sectional view of an alternate embodiment.
Figure 5B:
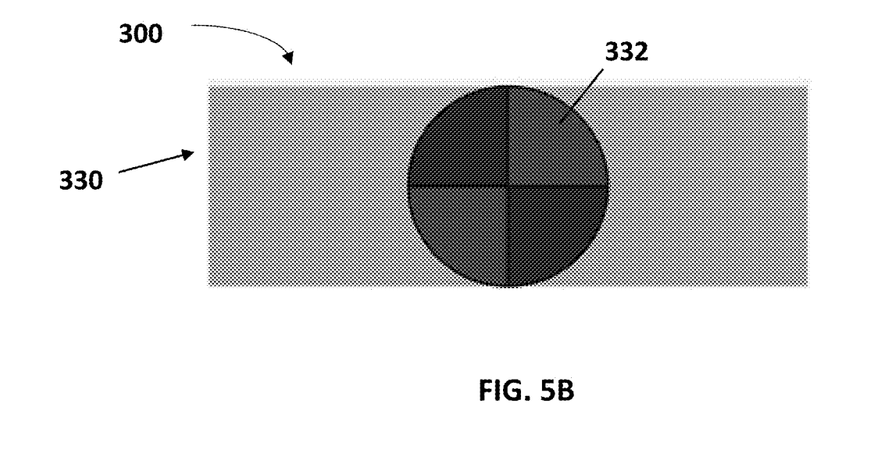
FIG. 5B shows a bottom view of the embodiment in FIG. 5A.

The embodiment 300 in FIGS. 5A-5B comprises 3 flexible layers—the middle layer 320 sandwiched between the anterior/top protective layer 310 and the posterior/bottom protective layer 330. The middle layer 320 can be made of one or more elastic materials, and it is made from a C-grain, light-density balsa sheet in this embodiment 300. If the embodiment 300 is attached to a user's joint and gets bent or twisted as the joint moves, the middle layer 320 is configured to kink, buckle, or even break when the joint position has been outside a predetermined allowable range so that the user would immediately know. How the middle layer 320 kinks, buckles, or breaks may also provide a clue to the user as to which direction the joint moves too much.

The dimensions of the middle layer 320 as well as the other layers 310 and 330 are preferably configured based on the characteristics of the materials adopted as well as the type of sport, the technique, and the user's skill level. In an embodiment similar to this embodiment 300 for monitoring the wrist of a golfer's leading arm, the middle layer is preferably a 1"×3"×1/32" C-grain, light-density balsa sheet for a beginner or a 1"×3"×1/64" C-grain, light-density balsa sheet for a more advanced player, and its protective layers should be configured accordingly. In yet another embodiment, the protective layers 310 & 330 may form a sheath and completely enclose the middle layer 320.

Furthermore, in this embodiment 300, the posterior protective layer 330 further includes a layer of transparent, skin-friendly adhesive 331, configured to couple to a user's skin at the joint. The posterior protective layer 330 may additionally comprise an indicator 332 configure to assist the user to properly place this embodiment 300. Ideally, when attached to a golfer's wrist, this embodiment 300 is placed equidistant to proximal and distal across the wrist crease lines and parallel to the long axis (X or radial/yaw Cartesian coordinate) of the leading arm.

While the invention has been described by means of specific embodiments, numerous modifications and variations could be made thereto by those ordinarily skilled in the art without departing from the scope and spirit disclosed herein. For instance, an embodiment may have different types, numbers, and arrangements of sensors from the embodiments 100 & 200; another embodiment may use different joint position measurement systems or optimal ranges; and so forth. In addition, various suitable materials may be adopted for the components in an embodiment, such as polyester or polyimide as a flex circuit substrate or different types of flexible yet brittle sheets as a middle layer, so that the embodiment is light-weight, flexible, and preferably eco-friendly. Furthermore, an embodiment may be disposable and thus preferably comprising low-cost, biodegradable components. Therefore, the invention is intended to cover all techniques, devices, or structures known in the art and not be limited in scope except by the purview of the appended claims.

The invention claimed is:

1. A wearable apparatus for sports training, comprising:
    (a) a processor;
    (b) a computer-readable medium communicably coupled to the processor and configured to store one or more optimal ranges of joint positions of a musculoskeletal joint of a user;

(c) a sensor communicably coupled to the processor and configured to detect a joint position of the user's musculoskeletal joint;

(d) a signaling component communicably coupled to the processor and configured to send a user detectable signal; and (e) a timer, wherein:

(1) the wearable apparatus is configured such that if the joint position of the user's musculoskeletal joint falls outside the one or more optimal ranges of joint positions of the user's musculoskeletal joint, the signaling component is activated to send the user detectable signal;

(2) the computer-readable medium is further configured to store one or more timed optimal ranges of joint positions of the user's musculoskeletal joint;

(3) each of the one or more timed optimal ranges is configured to comprise one of the one or more optimal ranges of joint positions of the user's musculoskeletal joint and a distinctive timecode;

(4) one of the distinctive timecodes is zero; and (5) the signaling component is activated when a current time stamp retrieved from the timer matches the distinctive timecode of one of the one or more timed optimal ranges, and the signaling component also being configured to be activated when the joint position of the user's musculoskeletal joint falls outside the one or more optimal ranges of joint positions of the one of the one or more timed optimal ranges.

2. The wearable apparatus of claim 1, wherein the wearable apparatus is configured such that the joint position of the user's musculoskeletal joint detected by the sensor is a relative angle between a distal side and a proximal side of the user's musculoskeletal joint.

3. The wearable apparatus of claim 1, further comprising an input/output component communicably coupled to the processor and configured to receive a user command.

4. The wearable apparatus of claim 3, wherein the input/output component is further configured to communicably couple the wearable apparatus to a device.

5. The wearable apparatus of claim 1, further comprising a flexible printed circuit board configured to support and electrically connect the processor, the computer-readable medium, the sensor, and the signaling component.

6. The wearable apparatus of claim 5, wherein the flexible printed circuit board is further configured to releasably couple to skin of the user at the user's musculoskeletal joint.

7. The wearable apparatus of claim 6, wherein the flexible printed circuit board further comprises a refastenable, skin-safe adhesive.

* * * * *